United States Patent [19]
Grimes et al.

[11] Patent Number: 6,132,720
[45] Date of Patent: *Oct. 17, 2000

[54] IMMUNOGENS AGAINST GONADOTROPIN RELEASING HORMONE

[75] Inventors: Stephen Grimes, Davis; Robert Scibienski, Woodland, both of Calif.

[73] Assignee: Aphton Corp., Woodland, Calif.

[ * ] Notice: This patent is subject to a terminal disclaimer.

[21] Appl. No.: 08/968,466

[22] Filed: Nov. 17, 1997

Related U.S. Application Data

[63] Continuation of application No. 08/188,223, Jan. 27, 1994, Pat. No. 5,688,506.

[51] Int. Cl.[7] .......................... A61K 38/00; A61K 39/00; A61K 39/385; A61K 39/38
[52] U.S. Cl. ..................... 424/184.1; 424/185.1; 424/193.1; 424/194.1; 424/198.1; 530/850; 530/300; 530/313; 530/326; 530/327; 530/328; 530/329; 530/810; 530/827; 530/852; 530/853; 530/854; 514/2; 514/800; 930/110; 930/130
[58] Field of Search ...................... 424/184.1, 185.1, 424/193.1, 194.1, 198.1; 530/850, 300, 313, 326, 327, 328, 329, 810, 827, 852–4; 514/2, 800; 930/110, 130

[56] References Cited

U.S. PATENT DOCUMENTS

| | | | |
|---|---|---|---|
| 3,963,691 | 6/1976 | Hoffman et al. | 260/112.5 |
| 4,201,770 | 5/1980 | Stevens | 424/177 |
| 4,302,386 | 11/1981 | Stevens | 260/112.5 |
| 4,384,995 | 5/1983 | Stevens | 260/112.5 |
| 4,526,716 | 7/1985 | Stevens | 260/112.5 |
| 4,608,251 | 8/1986 | Mia | 424/85 |
| 4,618,598 | 10/1986 | Conn . | |
| 4,676,981 | 6/1987 | Silversides | 424/85 |
| 4,691,006 | 9/1987 | Stevens | 530/324 |
| 4,780,312 | 10/1988 | Talwar . | |
| 4,795,634 | 1/1989 | Grimes et al. | 424/85.9 |
| 4,879,112 | 11/1989 | Silversides | 424/85.9 |
| 4,975,420 | 12/1990 | Silversides | 514/15 |
| 5,023,077 | 6/1991 | Gevas et al. . | |
| 5,036,047 | 7/1991 | Mia | 514/15 |
| 5,109,026 | 4/1992 | Hoskinson | 514/777 |
| 5,204,108 | 4/1993 | Illum | 424/434 |
| 5,324,512 | 6/1994 | Ladd et al. | 424/88 |
| 5,378,688 | 1/1995 | Nett et al. | 514/15 |
| 5,403,586 | 4/1995 | Russell-Jones | 424/192.1 |
| 5,413,990 | 5/1995 | Haviv et al. | 514/15 |
| 5,484,592 | 1/1996 | Meloen et al. | 424/185.1 |
| 5,488,036 | 1/1996 | Nett et al. | 514/15 |
| 5,506,207 | 4/1996 | Rivier | 514/15 |
| 5,508,383 | 4/1996 | Sauer et al. | 530/313 |
| 5,557,033 | 9/1996 | Halawani | 800/2 |
| 5,607,676 | 3/1997 | Gevas et al. . | |
| 5,609,870 | 3/1997 | Gevas et al. . | |
| 5,622,702 | 4/1997 | Gevas et al. . | |
| 5,633,248 | 5/1997 | Kato et al. | 514/212 |
| 5,648,340 | 7/1997 | Barnea . | |
| 5,661,126 | 8/1997 | Donahoe et al. | 514/12 |
| 5,684,145 | 11/1997 | Vander Zee et al. | 536/23.51 |
| 5,688,506 | 11/1997 | Grimes et al. | 424/184.1 |
| 5,759,551 | 6/1998 | Ladd et al. | 424/198.1 |
| 5,785,970 | 7/1998 | Gevas et al. . | |
| 5,843,446 | 12/1998 | Ladd et al. | 424/184.1 |

FOREIGN PATENT DOCUMENTS

| | | |
|---|---|---|
| 0293530 | 1/1987 | European Pat. Off. . |
| 0323769 | 11/1988 | European Pat. Off. . |
| 0293530 | 12/1988 | European Pat. Off. . |
| 0578293 | 1/1994 | European Pat. Off. . |
| 2593705 | 2/1986 | France . |
| 4003944 | 8/1991 | Germany . |
| 2228262 | 8/1990 | United Kingdom . |
| 8604243 | 7/1986 | WIPO . |
| 8606635 | 11/1986 | WIPO . |
| 8607383 | 12/1986 | WIPO . |
| 8800056 | 7/1987 | WIPO . |
| 9009799 | 9/1990 | WIPO . |
| 9102799 | 3/1991 | WIPO . |
| 9104052 | 4/1991 | WIPO . |
| 9116343 | 10/1991 | WIPO . |
| 9212247 | 7/1992 | WIPO . |
| 9212733 | 8/1992 | WIPO . |
| 9215330 | 9/1992 | WIPO . |
| 9219746 | 11/1992 | WIPO . |
| 9002187 | 2/1993 | WIPO . |
| 9302706 | 2/1993 | WIPO . |
| 9303058 | 2/1993 | WIPO . |
| 9319781 | 10/1993 | WIPO . |
| 9400590 | 1/1994 | WIPO . |
| 9425060 | 11/1994 | WIPO . |
| 9715316 | 5/1997 | WIPO . |
| 9715325 | 5/1997 | WIPO . |

OTHER PUBLICATIONS

Fraser, H.M. "Effects of antibodies to leutenizing hormone releasing hormone on reproductive functions in rodents", in Imm. Horm. Repr. Res., Nieschlag ed., pp. 107–117, 1975.

Stevens et al. "The identification of peptide sequences of human chorionic gonadotropin containing a conformational epitope", Imm. Set. 12: 11–18, 1986.

Conn, et al. "Gonadotropin–releasing hormone and its analogues", New Eng. J. Med. 2: 93–103, 1991.

McLachlan, et al. "Clinical aspects of LHRH analogues in gynecology: a review", J. Obs. Gyn. 93: 431–454.

Fraser, H.M. "Physiological effects of antibody to leuteinising hormone releasing hormone", in Physiological Effects of Immunity Against Reproductive Hormones, Edwards and Johnson, Eds. Cambridge Univ. Press, pp. 137–165, 1976.

Johnson, et al. "The regulation of gonadal function in essential reproduction", $3^{rd}$ Ed., pp. 101–154, 1988.

(List continued on next page.)

Primary Examiner—Nita Minnifield
Attorney, Agent, or Firm—White & Case LLP

[57] ABSTRACT

Immunogenic compositions capable of generating an immune response in mammals against GnRH are disclosed. The immunogenic compositions are effective in methods of treating gonadotropin and gonadal steroid hormone dependent diseases and immunological contraception of mammals.

4 Claims, 5 Drawing Sheets

OTHER PUBLICATIONS

Science and Technology, "Clipping the stork's wings", The Economist, pp. 73–78, Jan. 9, 1993.

Fraser, H.M. "Active immunization of stumptailed macaque monkeys against luteinizing hormone releasing hormone, and its effects on menstrual cycles, ovarian steroids and positive feedback", J. Rep. Imm. 5: 173–183, 1983.

Jeffcoate, et al. "Anti–RH Sera in the investigation of reproduction", in Physiological Effects of Immunity Against Reproductive hormones, Edwards and Johnson eds. Cambridge Univ. Press, pp. 121–136, 1976.

Singh et al. "The dominant role of amide group at C-termians for recognition of antibody" J. Ster Biochem 23: 801–2 (1985).

Filicori, M. et al. "GnRH agonists and antagonists, current clinical status", Drugs, 35: 63–82, 1988.

Burgus, et al. "GnRH agonists and antagonists, current clinical status" Drugs 35: 63–82 (1988).

Marini, et al. "A simple method for increasing hapten . . . " J. Immuno. 120: 57–63 (1989).

Ladd, A. "Progress in the development of anti–LHRH vaccine", Am. J. Reprod. Immunol. 29: 189–194, (1993).

Talwar, et al. "Recent development in immunocontraception", Am. J. Obstet. Gynocol. 157: 1075–1078, (1987).

Talwar, et al. "A birth control vaccine is on the horizon for family planning", Ann. Med. 25: 207–212, (1993).

Thau, R. "Anti–LHRH and anti–pituitary gonadotropin vaccines: their development and clinical applications", Scand. J. Immunol. 36: 127–130, (1992).

Winkel, post graduate Med. 95(6): 111–118 (May '94).

Jung et al. J. Cath. Med. Cell 43 (1): 161–70 (1990) (Abstract).

Dutta et al. Pharm. Med. 7(1): 9–28 (1993).

Tenover et al. J. Clin. Endocrinal. Metabol. 71/4:881–888 (1996).

Kaetsu et al. "Biodeg adable implant composites for local therapy" J. of Controlled Release 6 (1987) 249.

Milanovic et al "Effect of treatment with LMRH analogs containing . . . " J. Cancer Res. Ain–Oncol. 119 (1993) 273–278.

Vincze, B. et al.. "In Vivo Studies of the new gonadotropin–releasing hormone antagonist . . . " Cancer Detection and Prevention 20 (1996) 153–9.

Sad, S. et al. "Synthetic gonadotropin–releasing hormone . . . " Vaccine 11 (1993) 1145.

Rekasi et al. "Effect of Ruteinizing hormone–releasing hormone . . . " Endo 132 (1991) 1991–2000.

Palyi, I. et al. "Effect of gonadotropin–releasing hormone analysis and . . . " Cancer Detection and Prevention 20 (1996) 146–152.

RABBIT ANTI-GnRH ANTIBODY RESPONSES
TO A PEPTIDE CONJUGATE MIXTURE

MOUSE ANTI-GnRH ANTIBODY RESPONSES TO CONJUGATES WITH VARIOUS SUB. RATIOS

MEAN SERUM ANTI-GnRH Ab AND T LEVELS
IN MALE RABBITS IMMUNIZED AGAINST GnRH

PARAMETER ASSAYED

—*— ANTI-GnRH Ab    —□— TESTOSTERONE

Immunogen: Ser1+Ser10 conjugates (0.5 mg each) + nMDP (0.1 mg) with Montanide ISA 703 containing 1.8% AMS, given on day 0.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (iii) HYPOTHETICAL: NO (ix) FEATURE:
      (A) NAME/KEY: Peptide
      (B) LOCATION: 1..10
      (D) OTHER INFORMATION: /note= "Gonadotropin releasing
          hormone (GnRH)"

(ix) FEATURE:
      (A) NAME/KEY: Modified-site
      (B) LOCATION: 1
      (D) OTHER INFORMATION: /label= pGlu
          /note= "pyroglutamic acid (5-oxoproline)"

(ix) FEATURE:
      (A) NAME/KEY: Modified-site
      (B) LOCATION: 10
      (D) OTHER INFORMATION: /label= GlyNH2
          /note= "glycinamide"

(xi) SEQUENCE DESCRIPTION: SEQ ID NO:1:

Xaa His Trp Ser Tyr Gly Leu Arg Pro Xaa
1               5                   10

(2) INFORMATION FOR SEQ ID NO:2:

(i) SEQUENCE CHARACTERISTICS:
      (A) LENGTH: 16 amino acids
      (B) TYPE: amino acid
      (D) TOPOLOGY: linear

```
        (ii) MOLECULE TYPE: peptide (iii) HYPOTHETICAL: YES (ix) FEATURE:
             (A) NAME/KEY: Region
             (B) LOCATION: 1..10
             (D) OTHER INFORMATION: /note= "immunomimic"

(ix) FEATURE:
             (A) NAME/KEY: Region
             (B) LOCATION: 11..16
             (D) OTHER INFORMATION: /note= "spacer"

(ix) FEATURE:
             (A) NAME/KEY: Modified-site
             (B) LOCATION: 1
             (D) OTHER INFORMATION: /label= pGlu
                 /note= "pyroglutamic acid (5-oxoproline)"

(xi) SEQUENCE DESCRIPTION: SEQ ID NO:2:

Xaa His Trp Ser Tyr Gly Leu Arg Pro Gly Arg Pro Pro Pro Pro Cys
1               5                  10                  15

(2) INFORMATION FOR SEQ ID NO:3:

(i) SEQUENCE CHARACTERISTICS:
             (A) LENGTH: 10 amino acids
             (B) TYPE: amino acid
             (D) TOPOLOGY: linear (ii) MOLECULE TYPE: peptide (iii) HYPOTHETICAL: YES (v) FRAGMENT TYPE: N-terminal (ix) FEATURE:
             (A) NAME/KEY: Modified-site
             (B) LOCATION: 1
             (D) OTHER INFORMATION: /label= pGlu
                 /note= "pyroglutamic acid (5-oxoproline)"

(ix) FEATURE:
             (A) NAME/KEY: Peptide
             (B) LOCATION: 1..10
             (D) OTHER INFORMATION: /note= "immunomimic"

(xi) SEQUENCE DESCRIPTION: SEQ ID NO:3:

Xaa His Trp Ser Tyr Gly Leu Arg Pro Gly
1               5                  10

(2) INFORMATION FOR SEQ ID NO:4:

(i) SEQUENCE CHARACTERISTICS:
             (A) LENGTH: 6 amino acids
             (B) TYPE: amino acid
             (D) TOPOLOGY: linear (ii) MOLECULE TYPE: peptide (iii) HYPOTHETICAL: YES (v) FRAGMENT TYPE: C-terminal (ix) FEATURE:
             (A) NAME/KEY: Peptide
             (B) LOCATION: 1..6
             (D) OTHER INFORMATION: /note= "spacer"

(xi) SEQUENCE DESCRIPTION: SEQ ID NO:4:

Arg Pro Pro Pro Pro Cys
1               5
```

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: YES (ix) FEATURE:
        (A) NAME/KEY: Region
        (B) LOCATION: 1..7
        (D) OTHER INFORMATION: /note= "spacer"

(ix) FEATURE:
        (A) NAME/KEY: Region
        (B) LOCATION: 8..17
        (D) OTHER INFORMATION: /note= "immunomimic"

(ix) FEATURE:
        (A) NAME/KEY: Modified-site
        (B) LOCATION: 17
        (D) OTHER INFORMATION: /label= GlyNH2
              /note= "glycinamide"

(xi) SEQUENCE DESCRIPTION: SEQ ID NO:5:

Cys Pro Pro Pro Pro Ser Ser Glu His Trp Ser Tyr Gly Leu Arg Pro
1               5                   10                  15

Xaa (2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: YES (ix) FEATURE:
        (A) NAME/KEY: Modified-site
        (B) LOCATION: 1
        (D) OTHER INFORMATION: /label= pGlu
              /note= "pyroglutamic acid (5-oxoproline)"

(ix) FEATURE:
        (A) NAME/KEY: Region
        (B) LOCATION: 1..10
        (D) OTHER INFORMATION: /note= "immunomimic"

(ix) FEATURE:
        (A) NAME/KEY: Region
        (B) LOCATION: 11..17
        (D) OTHER INFORMATION: /note= "spacer"

(xi) SEQUENCE DESCRIPTION: SEQ ID NO:6:

Xaa His Trp Ser Tyr Gly Leu Arg Pro Gly Ser Ser Pro Pro Pro Pro
1               5                   10                  15

Cys (2) INFORMATION FOR SEQ ID NO:7:

(i) SEQUENCE CHARACTERISTICS:
        (A) LENGTH: 16 amino acids
        (B) TYPE: amino acid
        (D) TOPOLOGY: linear (ii) MOLECULE TYPE: peptide

```
        (iii) HYPOTHETICAL: YES (ix) FEATURE:
              (A) NAME/KEY: Region
              (B) LOCATION: 1..6
              (D) OTHER INFORMATION: /note= "spacer"

(ix) FEATURE:
              (A) NAME/KEY: Region
              (B) LOCATION: 7..16
              (D) OTHER INFORMATION: /note= "immunomimic"

(ix) FEATURE:
              (A) NAME/KEY: Modified-site
              (B) LOCATION: 16
              (D) OTHER INFORMATION: /label= GlyNH2
                  /note= "glycinamide"

(xi) SEQUENCE DESCRIPTION: SEQ ID NO:7:

Cys Pro Pro Pro Pro Arg Glu His Trp Ser Tyr Gly Leu Arg Pro Xaa
1               5                  10                  15

(2) INFORMATION FOR SEQ ID NO:8:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (iii) HYPOTHETICAL: YES (v) FRAGMENT TYPE: C-terminal (ix) FEATURE:
         (A) NAME/KEY: Peptide
         (B) LOCATION: 1..10
         (D) OTHER INFORMATION: /note= "immunomimic"

(ix) FEATURE:
         (A) NAME/KEY: Modified-site
         (B) LOCATION: 10
         (D) OTHER INFORMATION: /label= GlyNH2
             /note= "glycinamide"

(xi) SEQUENCE DESCRIPTION: SEQ ID NO:8:

Gly His Trp Ser Tyr Gly Leu Arg Pro Xaa
1               5                  10

(2) INFORMATION FOR SEQ ID NO:9:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (iii) HYPOTHETICAL: YES (v) FRAGMENT TYPE: N-terminal (ix) FEATURE:
         (A) NAME/KEY: Peptide
         (B) LOCATION: 1..7
         (D) OTHER INFORMATION: /note= "spacer"

(xi) SEQUENCE DESCRIPTION: SEQ ID NO:9:

Cys Pro Pro Pro Pro Ser Ser
1               5
```

-continued (2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: YES (v) FRAGMENT TYPE: C-terminal (ix) FEATURE:
        (A) NAME/KEY: Peptide
        (B) LOCATION: 1..7
        (D) OTHER INFORMATION: /note= "spacer"

(xi) SEQUENCE DESCRIPTION: SEQ ID NO:10:

Ser Ser Pro Pro Pro Pro Cys
1               5

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (ix) FEATURE:
        (A) NAME/KEY: Peptide
        (B) LOCATION: 1..6
        (D) OTHER INFORMATION: /note= "spacer"

(xi) SEQUENCE DESCRIPTION: SEQ ID NO:11:

Cys Pro Pro Pro Pro Arg
1           5

IMMUNOGENS AGAINST GONADOTROPIN RELEASING HORMONE

This application is a continuation of application Ser. No. 08/188,223, filed on Jan. 27, 1994 now U.S. Pat. No. 5,688,506.

BACKGROUND OF THE INVENTION

Gonadotropin Releasing Hormone ("GnRH", also known as Luteinizing Hormone Releasing Hormone, or "LHRH"), is of central importance to the regulation of fertility. Johnson M., Everitt B. *Essential Reproduction*, 3rd Edn. Blackwell Scientific Publications, 1988. In males and females, GnRH is released from the hypothalamus into the bloodstream and travels via the blood to the pituitary, where it induces the release of the gonadotropins, luteinizing hormone and follicle stimulating hormone, by gonadotroph cells. These two gonadotropins, in turn, act upon the gonads, inducing steroidogenesis and gametogenesis. Steroids released from the gonads into the circulation subsequently act upon various tissues.

The gonadotropin hormonal cascade can be halted by neutralization of the biological activity of GnRH. Fraser H. M. Physiological Effects of Antibody to Leutenizing Hormone Releasing Hormone. In: *Physiological Effects of Immunity Against Reproductive Hormones*, Edwards and Johnson, Eds. Cambridge University Press, 1976. As a consequence of GnRH neutralization, the gonadotropins and gonadal steroids are not released into the blood and their biological activities are thereby eliminated. By eliminating the biological activity of GnRH, the hormonal regulation of fertility is interrupted and gametogenesis ceases. GnRH neutralization halts the production of gametes. GnRH neutralization is thus an effective means of contraception.

A number of important diseases are affected by gonadotropins and gonadal steroid hormones, particularly the gonadal steroids. Such diseases include breast cancer, uterine and other gynecological cancers, endometriosis, uterine fibroids, prostate cancer and benign prostatic hypertrophy, among others. Removal of the gonadal steroid hormonal stimuli for these diseases constitutes an important means of therapy. An effective method of accomplishing this is by neutralizing GnRH, the consequence of which is the elimination of gonadal steroids that induce and stimulate these diseases. McLachlan R. I., Healy D. L., Burger G. B. 1986. Clinical Aspects of LHRH Analogues in Gynecology: a Review, *British Journal of Obstetrics and Gynecology*, 93:431–454. Conn P. M., Crowley W. F. 1991. Gonadotropin-Releasing Hormone and Its Analogs, *New England Journal of Medicine*. 324:93–103. Filicori M., Flamigni C. 1988. GnRH Agonists and Antagonists, Current Clinical Status. *Drugs*. 35:63–82.

One effective means of neutralizing GnRH is the induction or introduction of anti-GnRH antibodies in the host or patient. Such antibodies can be induced by active immunization with GnRH immunogens or by passive immunization by administering anti-GnRH antibodies. Fraser H. M. Physiological Effects of Antibody to Leutenizing Hormone Releasing Hormone. In: *Physiological Effects of Immunity Against Reproductive Hormones*, Edwards and Johnson, Eds. Cambridge University Press, 1976. Since anti-GnRH antibodies can neutralize the biological activity of GnRH, immunization constitutes an important approach towards treating diseases dependent upon gonadal steroids and other reproductive hormones as well as a means to regulate mammalian fertility.

GnRH has the same amino acid sequence in all mammals (pGlu-His-Trp-Ser-Tyr-Gly-Leu-Arg-Pro-GlyNH$_2$) (SEQ ID NO.: 1 in the Sequence Listing), thus a single immunogen would be effective in all mammalian species, including humans. Active immunization against GnRH, however, has not been practicable due to deficiencies associated with the GnRH immunogens. The prior art anti-GnRH immunogens are not of sufficient potency, and therefore must be administered repeatedly to induce effective levels of anti-GnRH antibodies. In addition, they have not proven to be reliable, in terms of inducing anti-GnRH antibodies in an acceptable portion of the immunized population.

SUMMARY OF THE INVENTION

The present invention, concerns improved immunogens against GnRH that induce neutralizing titers of anti-GnRH antibodies in response to a single administration of immunogen in all of the immunized populations that we have studied. The immunogens of the invention may thus be used to treat steroid dependent diseases and may also be used as immunocontraceptives to regulate fertility.

The immunogens of the present invention are peptides composed of two functional regions: the immunomimic region and a spacer region. The function of the immunomimic which immunologically crossreacts with GnRH is to induce antibodies that bind to the targeted hormone. The spacer element of the peptide serves as a link through which the immunomimic is attached to an immunological carrier, such as diphtheria toxoid ("DT") and also affects the immune response generated by the vaccinated mammal against the immunomimic. For example, in a specific embodiment of the invention, the immunogen peptide has the sequence: pGlu-His-Trp-Ser-Tyr-Gly-Leu-Arg-Pro-Gly-Arg-Pro-Pro-Pro-Pro-Cys (SEQ ID NO: 2 in the Sequence Listing). In this ("GnRH(1-10)-Arg10") peptide, the sequence pGlu-His-Trp-Ser-Tyr-Gly-Leu-Arg-Pro-Gly— (SEQ ID NO: 3 in the Sequence Listing), comprises the immunomimic of GnRH. The remainder of the peptide's sequence, —Arg-Pro-Pro-Pro-Pro-Cys (SEQ ID NO: 4 in the Sequence Listing), constitutes the spacer, which is attached to amino acid number 10 of the GnRH immunomimic.

A preferred embodiment of the invention concerns two peptide immunomimics of GnRH that are associated with four spacer sequences. Methods of coupling these peptides to immunological carriers, such as DT, to yield anti-GnRH immunogens are provided. The immunogens may be used singly or in combination to induce anti-GnRH antibody responses in the vaccinated mammal. As compared to the prior art anti-GnRH immunogens, the immunogens of the present invention induce a biologically effective immune response following a single administration of immunogen in all of the immunized animals tested. The immunogens can be administered in different physical forms, including soluble and precipitate. The immunomimic spacer peptides of this invention can be coupled to immunological carriers over a wide range of peptide to carrier substitution ratios and yield effective immunogens.

The invention also concerns methods of treating gonadotropin and gonadal steroid hormone dependent diseases and cancers by immunization with the immunogens of the invention. A specific embodiment of the invention concerns a method of immunological contraception in mammals comprising the administration of the inventive immunogens.

DETAILED DESCRIPTION OF THE INVENTION

EXAMPLE 1

Figure 1:
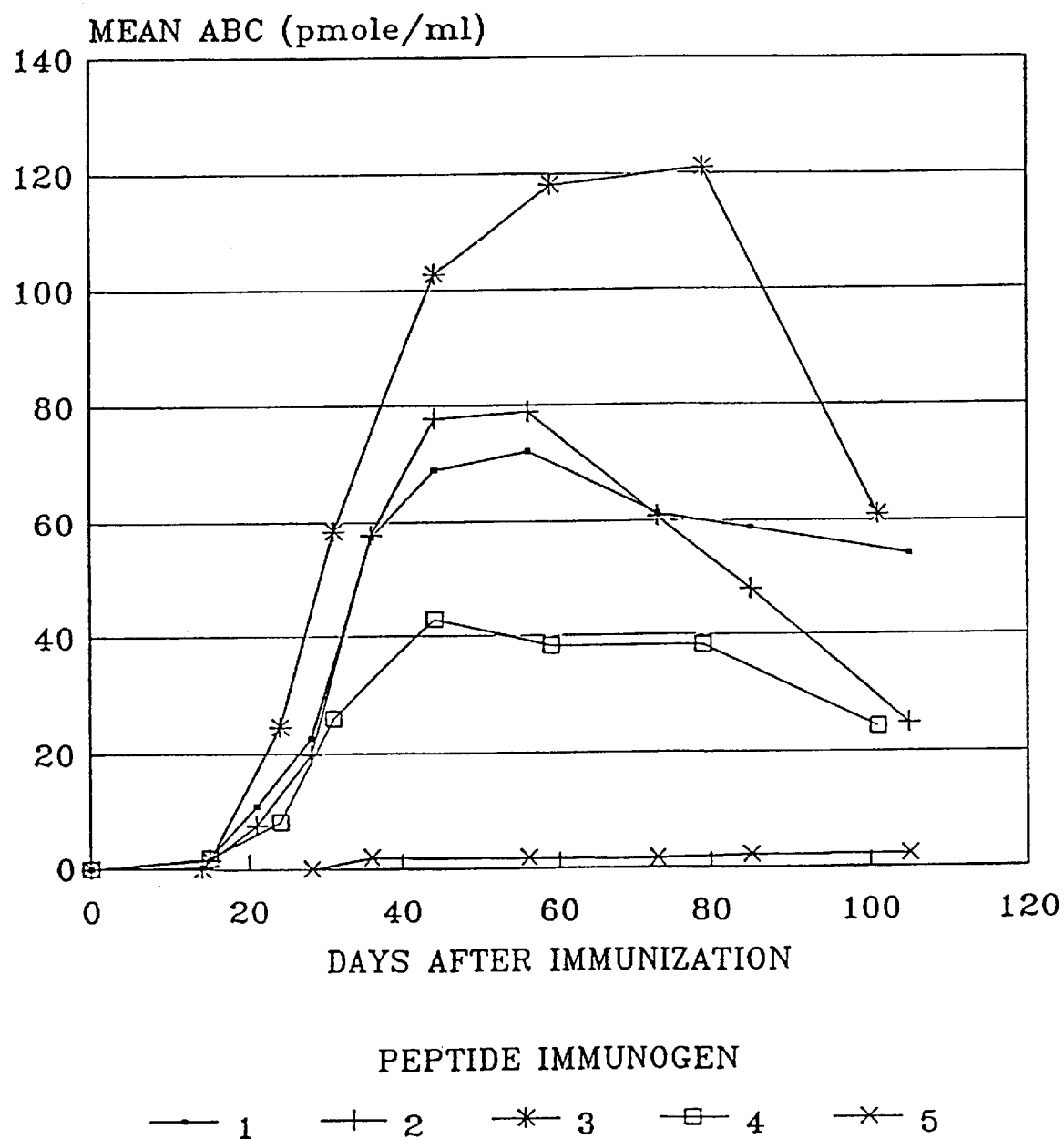
FIG. 1: Depicts anti-GnRH antibody responses to the administration of the inventive immunogens comprising peptides 1–4 and the comparative prior art anti-GnRH immunogen, peptide 5 as measured by mean antigen binding capacities ("ABC") in pico moles per milliliter with respect to days after immunization in immunized rabbits.

Peptides with the amino acid sequences listed in Table 1 were synthesized and prepared by standard solid phase synthesis methods. Each peptide was characterized as to amino acid content and purity.

TABLE 1

| Peptide | Designation | Amino Acid Sequence |
| --- | --- | --- |
| 1 | GnRH(1-10)-Ser1 | Cys—Pro—Pro—Pro—Pro—Ser—Ser—Glu—His—Trp—Ser—Tyr—Gly—Leu—Arg—Pro—Gly(NH$_2$)(SEQ ID NO: 5 in the Sequence Listing) |
| 2 | GnRH(1-10)-Ser10 | pGlu—His—Trp—Ser—Tyr—Gly—Leu—Arg—Pro—Gly—Ser—Ser—Pro—Pro—Pro—Pro—Cys (SEQ ID NO: 6 in the Sequence Listing) |
| 3 | GnRH(1-10)-Arg1 | Cys—Pro—Pro—Pro—Pro—Arg—Glu—His—Trp—Ser—Tyr—Gly—Leu—Arg—Pro—Gly(NH$_2$) (SEQ ID NO: 7 in the Sequence Listing) |
| 4 | GnRH(1-10)-Arg10 | pGlu—His—Trp—Ser—Tyr—Gly—Leu—Arg—Pro—Gly—Arg—Pro—Pro—Pro—Pro—Cys (SEQ ID NO: 2 in the Sequence Listing) |

Each of peptides 1–4 contains an immunomimic of GnRH that is either preceded by or followed by a spacer. Two immunomimics of GnRH were used: pGlu-His-Trp-Ser-Tyr-Gly-Leu-Arg-Pro-Gly— (SEQ ID NO: 3 in the Sequence Listing), (peptides 2 and 4 Table 1) wherein the spacer was attached through the carboxy terminal end of GnRH (amino acid #10); and, —Glu-His-Trp-Ser-Tyr-Gly-Leu-Arg-Pro-Gly(NH$_2$) (SEQ ID NO: 8 in the Sequence Listing), (peptides 1 and 3 Table 1) wherein the spacer was attached at the amino terminal end of GnRH (amino acid #1).

The four spacers set forth in Table 2 were used.

TABLE 2

| Spacer Designation | Amino Acid Sequence |
| --- | --- |
| Ser 1 | Cys—Pro—Pro—Pro—Pro—Ser—Ser— (SEQ ID NO: 9 in the Sequence Listing) |
| Ser 10 | —Ser—Ser—Pro—Pro—Pro—Pro—Cys (SEQ ID NO: 10 in the Sequence Listing) |
| Arg 1 | Cys—Pro—Pro—Pro—Pro—Arg— (SEQ ID NO: 11 in the Sequence Listing) |
| Arg 10 | —Arg—Pro—Pro—Pro—Pro—Cys (SEQ ID NO: 4 in the Sequence Listing) |

The numerals 1 and 10 in the spacer designation refer to the GnRH amino acid number to which the spacer is attached. While these spacer regions of the molecules have been set forth separately in Table 2, in the preferred embodiment of the invention the peptide is synthesized as one continuous peptide sequence molecule.

Each of these peptides 1–4 of Table 1 was conjugated to amino groups present on a carrier such as Diphtheria Toxoid ("DT") via the terminal peptide cysteine residue utilizing heterobifunctional linking agents containing a succinimidyl ester at one end and maleimide at the other end of the linking agent.

To accomplish the linkage between any of the Peptides 1–4 above and the carrier, the cysteine of the peptide was first reduced. The dry peptide was dissolved in 0.1 M sodium phosphate buffer (degassed), pH 8.0, with a thirty molar excess of dithiothreitol ("DTT"). The solution was stirred under a water saturated nitrogen gas atmosphere for three hours at room temperature. An additional 15 molar excess DTT was added and the mixture was stirred an additional hour at room temperature under water saturated nitrogen gas. The peptide containing reduced cysteine was separated from the other components by chromatography at 4° C. over a G10 Sephadex column equilibrated with 0.2 M acetic acid. The peptide was lyophilized and stored under vacuum until used.

The DT was activated for coupling to the peptide by treatment with the heterobifunctional linking agent epsilon-maleimidocaproic acid N-hydroxysuccinimide ester ("EMCS"), in proportions sufficient to achieve activation of approximately 25 free amino groups per $10^5$ molecular weight of DT. In the specific instance of DT, this amounted to the addition of 6.18 mg of EMCS (purity 98%) to each 20 mg of DT.

Activation of DT was accomplished by dissolving each 20 mg aliquot of DT in 1 ml of 0.5 M sodium phosphate buffer, pH 6.6. Aliquots of 6.18 mg EMCS were dissolved into 0.2 ml of dimethylformamide. Under darkened conditions, the EMCS was added dropwise in 50 microliter ("$\mu$l") amounts to the DT with stirring. After 90 minutes incubation at room temperature in darkness, the mixture was chromatographed at 4° C. on a G50 Sephadex column equilibrated with 0.1 M sodium citrate buffer, pH 6.0, containing 0.1 mM ethylenediaminetetraacetic acid disodium salt ("EDTA"). (Column= 1.5×120 cm; flow rate=8 ml/hr; fraction size=2 ml). The fractions' $A_{260}$ were determined using a spectrophotometer, enabling the fractions containing DT to be identified.

Fractions containing the EMCS activated DT were pressure concentrated over a PM 10 ultrafiltration membrane under nitrogen gas in conditions of darkness. The protein content of the concentrate was determined by the BCA method (PIERCE, Ill., USA). The EMCS content of the carrier was determined by incubation of the activated DT with cysteine-HCl followed by reaction with 100 μl of 10 mM Elman's Reagent (5, 5, dithio-bis (2-nitrobenzoic acid)). The optical density difference between a blank tube containing cysteine-HCl and the sample tube containing cysteine-HCl and carrier was translated into EMCS group content by using the molecular extinction coefficient of $13.6×10^3$ for 5-thio-2-nitro-benzoic acid at 412 nm.

The reduced cysteine content ("-SH") of the peptide was also determined utilizing Elman's Reagent. Approximately 1 mg of peptide was dissolved in 1 ml of nitrogen gas saturated water and a 0.1 ml aliquot of this solution was reacted with Elman's Reagent. Utilizing the molar extinction coefficient of 5-thio-2-nitro-benzoic acid ($13.6×10^3$), the free cysteine -SH was calculated.

The reduced peptide was then coupled to the activated DT. An amount of peptide containing sufficient free -SH to react with a selected proportion of the EMCS activated amino groups on the DT was dissolved in 0.1 M sodium citrate buffer, pH 6.0, containing 0.1 mM EDTA, and added dropwise to the EMCS activated DT under darkened conditions. After all the peptide solution had been added to the activated DT, the mixture was incubated overnight in the dark under a water saturated nitrogen gas atmosphere at room temperature.

The conjugate of the peptide linked to DT via EMCS was separated from other components of the mixture by low pressure chromatography at 4° C. over a G50 Sephadex column equilibrated with 0.2 M ammonium bicarbonate (column=1.5×120 cm, flow rate=1.8 ml/15 min., fraction size=1.8 ml). The conjugate eluted in the column void volume (detected by $A_{280}$ measurements) and was lyophilized and stored desiccated at −20° C. until used.

The conjugate may be characterized as to peptide content by a number of methods known to those skilled in the art including weight gain, amino acid analysis, etc. Various substitution ratios of peptide to DT were accurately and reproducibly obtained by (1) varying the quantity of EMCS added to activate the DT, and/or, (2) varying the quantity of reduced peptide added to the EMCS activated DT. For example, the activation of DT with a ratio of 31 moles EMCS to 1 mole of 100,000 molecular weight DT adds 12±2 EMCS groups per 100,000 molecular weight of DT. The addition of 14 peptide groups per 100,000 molecular weight of this activated DT resulted in a substitution ratio of 12±2 peptides per 100,000 molecular weight of DT. Conjugates of Peptides 1–4 to DT produced by these methods were determined by amino acid analysis to have 4–30 moles of peptide per $10^5$ MW of DT. All of the conjugates were considered suitable as immunogens for immunization of test animals.

EXAMPLE 2

For comparative purposes a prior art GnRH immunogen ("peptide 5") was constructed wherein the peptide immunomimic of GnRH did not contain a spacer element. Peptide 5 had the sequence: Glu-His-Trp-Ser-Tyr-Gly-Leu-Arg-Pro-GlyNH$_2$ (SEQ ID NO: 8 in the Sequence Listing).

The peptide was activated with m-Maleimidobenzoyl N-Hydroxysuccinimide Ester ("MBS"). 20.0 mg of [glu 1]-GnRH were dissolved in 1.0 ml of N,N-Dimethylformamide ("DMF"). To this solution was added 5.31 mg MBS dissolved in 1.0 ml DMF. The combined solution was stirred overnight at room temperature in the dark.

40.0 mg of DT was dissolved in 10.0 ml of Sodium Carbonate Buffer (0.2 M, pH=9.0), containing 2.2 mg of 2-Iminothiolane HCl ("2-IT"). The solution containing the MBS-activated GnRH was then slowly added to the DT/2-IT solution, and the mixture was stirred slowly for 8 hours at room temperature in the dark.

The conjugate was purified by column chromatography over Sephadex G50 (column: 1.5×100 cm; buffer: Ammonium Bicarbonate, 0.2 M; fractions: 2.6 ml, every 15 minutes) with identification of the fractions containing conjugate by spectrophotometry ($A_{254}$). G50 purified conjugate was lyophilized and stored desiccated at −20° C. until used. The peptide DT substitution ratio of the Immunogen 5 conjugate was determined by amino acid analysis to be 13 peptides per $10^5$ molecular weight of DT.

EXAMPLE 3

Different groups of female rabbits were each immunized with one of the conjugates, peptides 1–5 of Examples 1 and 2. Each conjugate was dissolved to a concentration of 2.0 mg/ml in phosphate buffered saline (0.2 M, pH=7.2) containing 200 μg/ml of norMDP adjuvant. The conjugates comprising peptides 1,2,3 and 4 of Example 1 did not completely dissolve in the buffer; the conjugate of peptide 5 of Example 2 did completely dissolve in the buffer. Each mixture was emulsified with an equal volume of Squalene-Arlacel (4:1 ratio, volume of Squalene: volume of Arlacel) to prepare an immunogen formulation which contained 1.0 mg/ml conjugate and 100 μg/ml norMDP. 1.0 ml of immunogen was injected into each rabbit, administered into the rear leg muscles (2 sites, 0.5 ml/site), on day 0 of the test. Blood was collected from each rabbit prior to immunization on day 0, and on selected days thereafter. Serum was prepared from each blood sample and stored frozen at −20° C. until utilized in assays to determine the presence of anti-GnRH antibodies.

A liquid phase Radioimmunoassay (RIA) was used to detect and quantify anti-GnRH antibodies. In the RIA, 0.04, 0.2, 1.0 or 5.0 μl aliquots of antiserum were incubated with approximately 150 fmole of 3H labeled GnRH (specific activity=53.2 Ci/mmole) in a total volume of 400 μl. Dilutions were made in FTA Hemagglutination Buffer (BBL, Becton Dickinson Microbiology Systems, MD, USA) containing 1% bovine serum albumin. The antisera were incubated with labeled hormone for 2 hours at room temperature. A 0.1 ml aliquot of heat inactivated (56° C., 30 min) fetal calf serum (cooled to 2–8° C.) was then added to each tube, following which the antibody-hormone complexes were precipitated by the addition of 0.5 ml of 25% polyethylene glycol (MW=8,000 gm/mole) (cooled to 2–8° C.). The precipitates were pelleted by centrifugation (30 minutes at 1500×g), the supernatants were discarded, and the pellets were counted by liquid scintillation counting to measure the quantity of radioactivity contained therein. Antigen binding capacities (ABC) for each antiserum were then determined from the amount of radioactive hormone precipitate after subtraction of nonspecific background binding (determined by preincubation of the antisera dilution with excess amounts (~$10^5$ fold) of the hormone). Inhibition of the antisera with the excess quantity of unlabeled hormone also established the specificity of the antisera for GnRH. Serum taken from the rabbits prior to immunization served as nonimmunized (normal) controls.

The mean ABCs measured in the sera from rabbits immunized with the conjugated peptides of Examples 1 and 2 are shown in Table 3 and in FIG. 1. As the results show, a single administration of the immunogens comprising peptides 1,2,3 and 4 of Example 1 induced rapid and potent antibody responses against GnRH.

TABLE 3

RABBIT ANTI-GNRH ANTIBODY RESPONSES INDUCED BY ONE ADMINISTRATION OF PEPTIDE CONJUGATE

| Peptide | Peptide:DT Substitution Ratio | Rabbit Sera ABC (mean) [pmoles/ml] | | | | | | | | |
|---|---|---|---|---|---|---|---|---|---|---|
| | | Day 0 | Day 14 | Day 21 | Day 28 | Day 36 | Day 44 | Day 56 | Day 73 | Day 85 | Day 105 |
| 1 | 13 | 0 | 0.30 | 10.83 | 22.63 | 57.23 | 68.93 | 72.13 | 61.23 | 58.73 | 54.03 |
| 2 | 13 | 0 | 0.27 | 7.52 | 19.83 | 57.63 | 77.83 | 78.73 | 60.83 | 47.90 | 24.93 |
| 5 | 13 | 0 | 0 | | 0 | 1.78 | | 1.60 | 1.51 | 2.00 | 2.10 |
| | | Day 0 | Day 15 | Day 24 | Day 31 | | Day 44 | Day 59 | | Day 79 | Day 101 |
| 3 | 11 | 0 | 1.53 | 24.59 | 58.31 | | 102.71 | 118.16 | | 120.99 | 61.00 |
| 4 | 13 | 0 | 1.77 | 8.90 | 26.03 | | 42.88 | 38.25 | | 38.30 | 24.35 | n = 5 rabbits for Peptides 1, 2, 3 and 4. n = 6 rabbits for peptide 5.

By comparison, the anti-GnRH response induced by a single administration of the peptide 5 immunogen of Example 2 induced a minimal response. This is not because the conjugate constructed with peptide 5 is a poor immunogen; when administered in additional booster immunizations several weeks after the first immunization, the peptide 5 conjugate induces effective levels of anti-GnRH antibodies (of approximately 12–18 pmole/ml ABC). In this regard, the peptide 5 conjugate behaves similarly to standard GnRH immunogens. However, the conjugate constructed with peptide 5 requires more than one administration, induces lower levels of anti-GnRH antibodies, and takes a longer time to elicit effective antibody levels than do the conjugates of peptides 1–4 of Example 1.

These results also demonstrate the critical contribution of the spacer to the immunogenicity of peptides 1,2,3 and 4 of Example 1. Peptide 5 bears the same immunomimic of GnRH as peptides 1 and 3, yet peptide 5 is inferior as an immunogen. This is because peptide 5 does not contain a spacer sequence, which is present in peptides 1 and 3. Thus, the presence of the spacers in peptides 1,2,3 and 4 of Example 1 makes a critical contribution to their enhanced immunogenicity.

EXAMPLE 4

Figure 2:
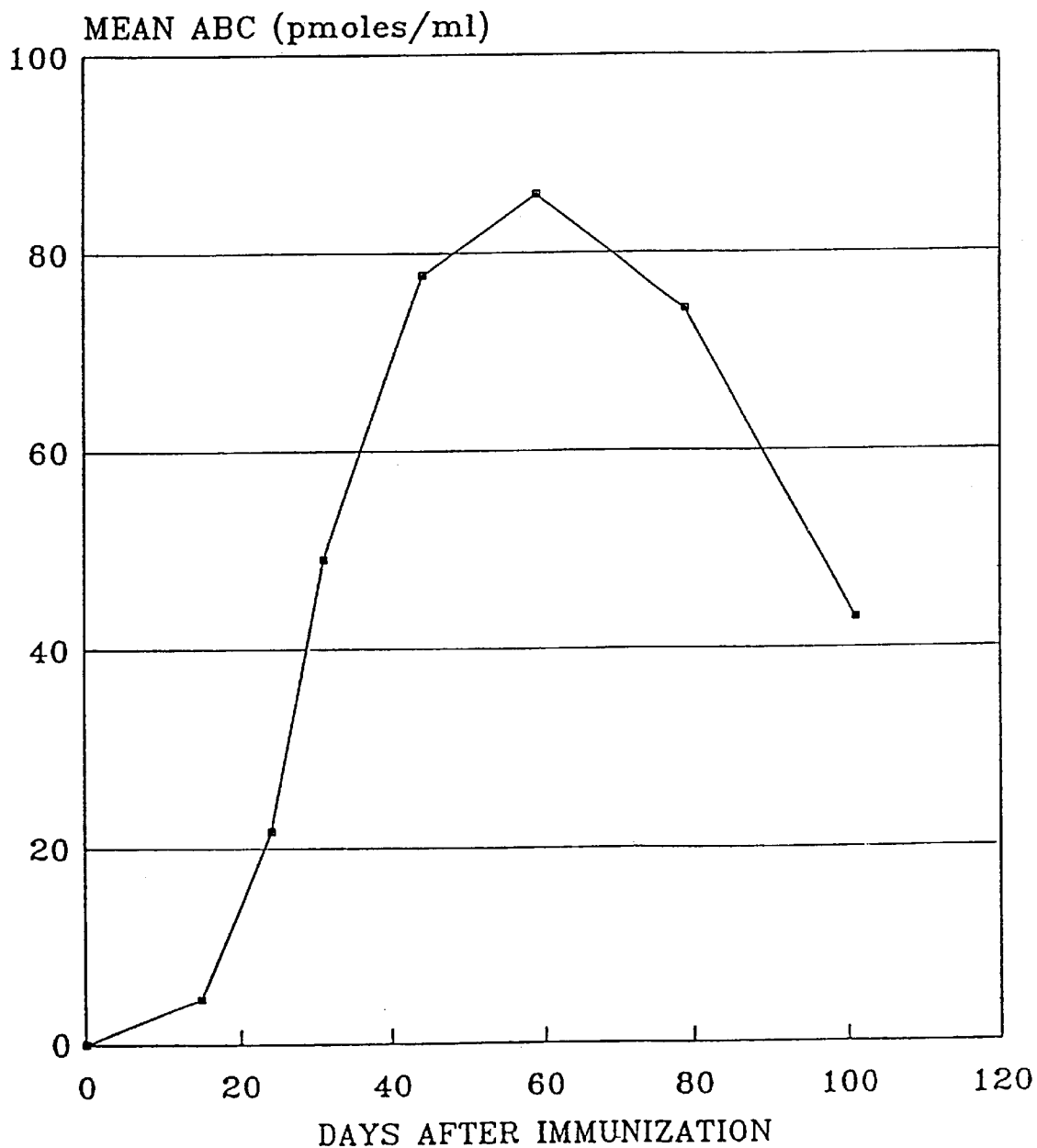
FIG. 2: Depicts the antibody response to immunization with an immunogen comprising a mixture of peptides 3 and 4 as measured by mean ABC with respect to days after immunization.

Conjugates comprising peptides 3 and 4 of Example 1 were mixed 1:1 to give a protein concentration of 2.0 mg/ml in PBS. The mix was then prepared as immunogen and injected into rabbits, as in Example 3. The sera were tested for anti-GnRH antibody by the RIA of Example 3. The results are shown in Table 4 and FIG. 2.

As can be seen from Table 4, effective levels of antibody were induced by the combined administration of the peptide 3 and 4 conjugates. Both peptide components contributed almost equally to the induction of the anti-GnRH antibodies, as shown by antibody specificity testing. The GnRH (1-10)-Arg1 peptide induced antibodies directed predominantly against the carboxy terminal end of GnRH, while the GnRH (1-10)-Arg10 peptide induced antibodies directed against the amino terminal end of GnRH. Thus, conjugates comprising these peptides can be mixed to yield immunogens that induce antibodies against both ends of the target molecule.

EXAMPLE 5

When the peptides of Example 1 are conjugated to DT and prepared as described in Example 1, a proportion of the product is present as a precipitate. The formation of the precipitate is dependent upon various physical parameters, including concentration of conjugate, pH and salt concentration. We prepared a conjugate of peptide 2 of Example 1 to DT as described in Example 1. From this we prepared three fractions of conjugate, based upon solubility. The conjugate was stirred in 0.01 M phosphate buffer pH=7.2 and the insoluble material was collected by centrifugation as Fraction #1. To the soluble material we added NaCl (to 0.5 M) and adjusted the pH to 6.0 with 0.1 M HCl, which yielded additional precipitate that we collected as Fraction #2. The remaining soluble material served as Fraction #3. Each fraction was lyophilized. The percent recoveries (from the 15 mg of starting material) were: Fraction-1, 36%; Fraction-2, 15%; Fraction-3, 27%; lost, 22%.

Each of the fractions 1–3 were injected into a group of mice, at 6 mice/group. (100 µg conjugate/mouse, with 25 µg nMDP, in 0.1 ml of a 1:1 mixture of FTA buffer (containing conjugate+adjuvant) to squalene-arlacel, i.p.). The mice received a single injection of immunogen, after which sera samples were obtained at intervals and tested for anti-GnRH

TABLE 4

RABBIT ANTI-GNRH RESPONSES INDUCED BY ONE ADMINISTRATION OF A MIXTURE OF PEPTIDE CONJUGATES
ABC (mean ± s.e.) [moles/ml]

Figure 3:
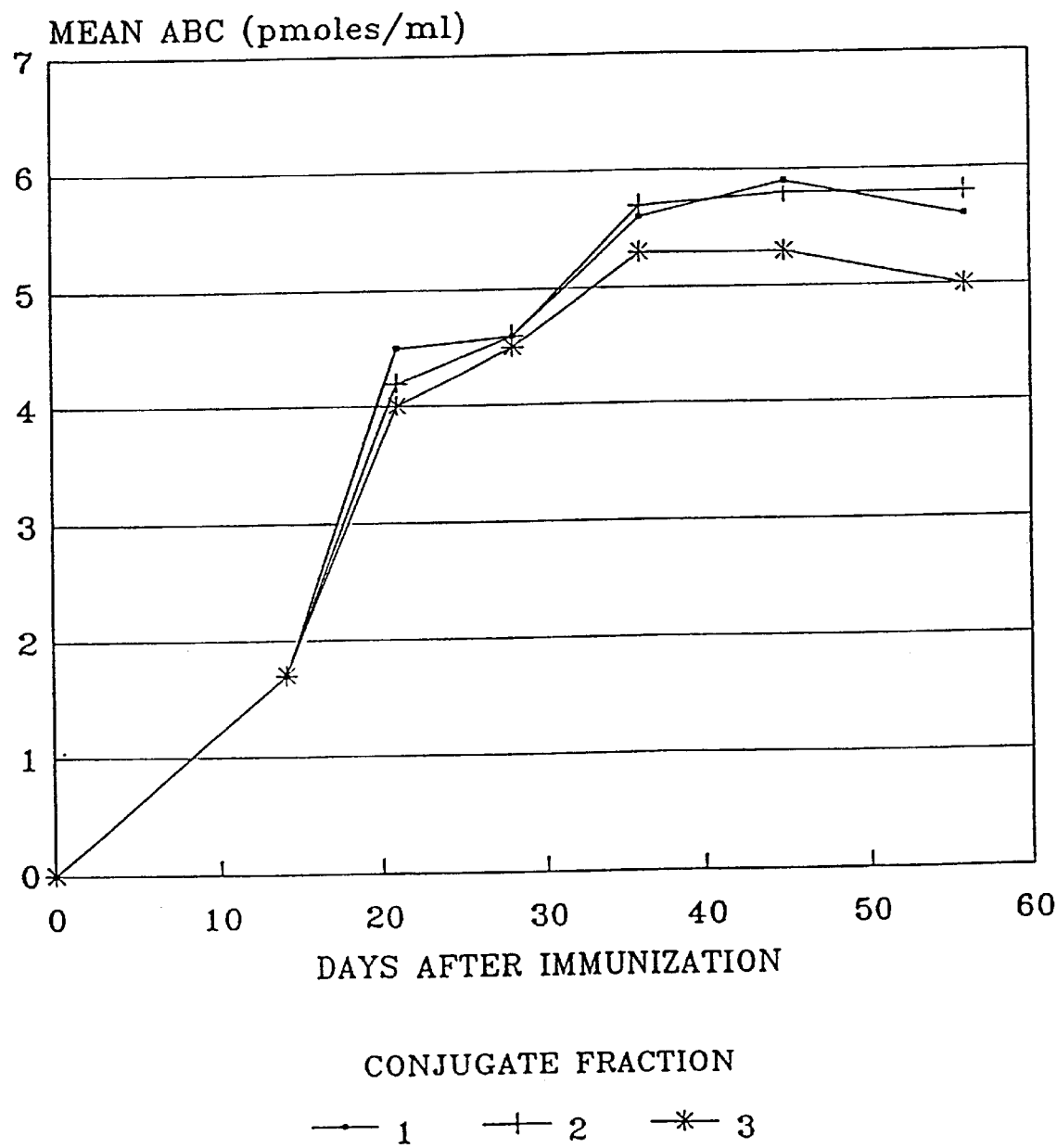
FIG. 3: Depicts the results of immunizations in mice as measured by a mean ABC with respect to days after immunization after immunization with fractions of a preparation of peptide 2 immunogens fractionated on the basis of solubility.

| Day of Test | 0 | 15 | 24 | 31 | 44 | 59 | 79 | 101 |
|---|---|---|---|---|---|---|---|---|
| ABC | 0 | 4.6 ± 0.7 | 21.6 ± 3.3 | 49.0 ± 9.9 | 77.8 ± 13.0 | 86.0 ± 21.0 | 74.3 ± 22.0 | 43.0 ± 12.0 | antibody by the RIA of Example 3. The results of this test are shown in Table 5 and in FIG. 3.

TABLE 5

ANTI-GnRH RESPONSES OF MICE TO SOLUBILITY FRACTIONS OF CONJUGATE

| Conjugate | ABC (mean ± s.e.) [moles/ml] | | | | | | |
|---|---|---|---|---|---|---|---|
| Fraction | Day 0 | Day 14 | Day 21 | Day 28 | Day 36 | Day 45 | Day 56 |
| 1 | 0 | 1.7 ± 0.3 | 4.5 ± 0.4 | 4.6 ± 0.4 | 5.6 ± 0.4 | 5.9 ± 0.5 | 5.6 ± 0.4 |
| 2 | 0 | 1.7 ± 0.4 | 4.2 ± 0.3 | 4.6 ± 0.2 | 5.7 ± 0.2 | 5.8 ± 0.2 | 5.8 ± 0.2 |
| 3 | 0 | 1.7 ± 0.3 | 4.0 ± 0.3 | 4.5 ± 0.3 | 5.3 ± 0.3 | 5.3 ± 0.3 | 5.0 ± 0.3 |

As the results show, each mouse group produced equally potent anti-GnRH antibody responses. This demonstrates that despite variances in the solubility of conjugates produced from the peptide of Example 1, the soluble and insoluble forms can be administered as immunogens and are of equivalent immunogenicity.

EXAMPLE 6

We constructed conjugates of peptides 1 and 2 of Example 1 to DT as described in Example 1. By varying the quantities of reduced peptide added to DT, we constructed conjugates with different peptide:DT substitution ratios. The substitution ratios, determined by amino acid analysis of the conjugates are shown in Table 6:

TABLE 6

| Conjugate Number | Peptide Used (from Example 1) | Peptide:DT Substitution Ratio |
|---|---|---|
| 6.1 | 1 | 4.7 |
| 6.2 | 1 | 13.1 |
| 6.3 | 1 | 25.9 |
| 6.4 | 2 | 5.1 |
| 6.5 | 2 | 12.8 |
| 6.6 | 2 | 30.1 |

Figure 4:
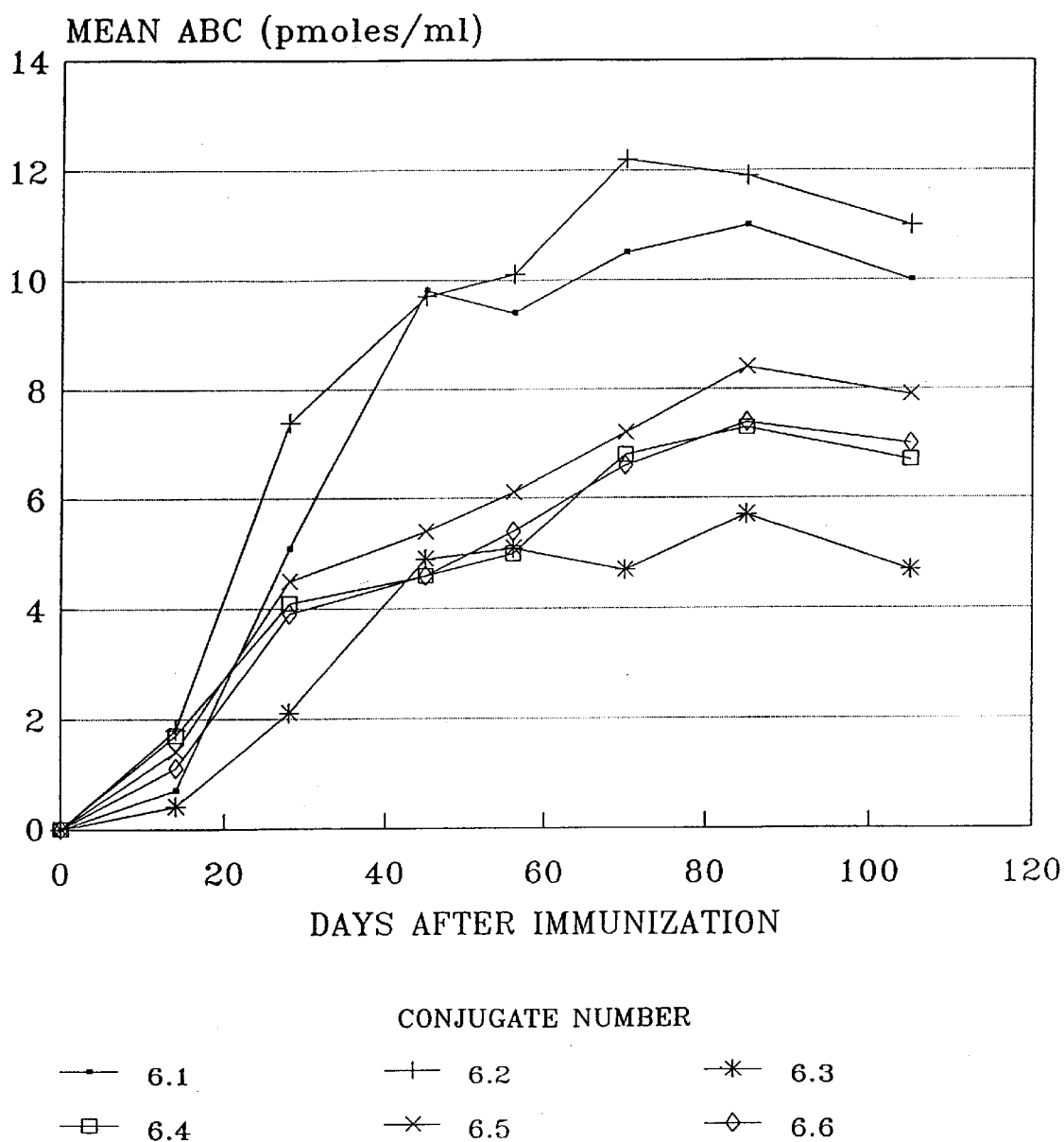
FIG. 4: Depicts antibody responses in mice as measured by mean ABC with respect to days after immunization when immunized with various conjugates of peptides 1 and 2 at different peptide: DT substitution ratios.

Mice were immunized with each conjugate preparation. The immunization and subsequent assay procedures were identical to those described in Example 5 (6 mice/group). The results of this test are shown in Table 7 and in FIG. 4.

EXAMPLE 7

We constructed conjugates of peptides 1 and 2 of Example 1 to DT as described in Example 1. The peptide:DT substitution ratio for peptide 1 (GnRH(1-10)-Ser1) was 13.1:1 and the ratio for peptide 2 (GnRH(1-10)-Ser10) was 12.8:1.

We prepared immunogen by emulsifying aqueous phase (containing a mixture of the two conjugates plus norMDP in PBS) with oily vehicle as described in Example 3. The oily vehicle used was Montanide ISA 703 containing 1.8% aluminum monostearate. "Montanide ISA 703 AMS" is manufactured and sold by SEPPIC, Inc. (Paris, France). The final concentrations of the active components in the immunogen were: GnRH (1-10)-Ser1-DT=0.5 mg/ml; GnRH (1-10)-Ser10-DT=0.5 mg/ml; norMDP=0.1 mg/ml. 1.0 ml of immunogen was injected into each of 3 male rabbits, administered to the rear leg muscles (2 sites/rabbit, 0.5 ml/site), on day 0 of the test. Blood was collected from each rabbit prior to immunization and on selected days thereafter. Serum was prepared from each blood sample and stored frozen at −20° C. until utilized in assays to determine the presence of anti-GnRH antibodies (as described in Example 3).

Figure 5:
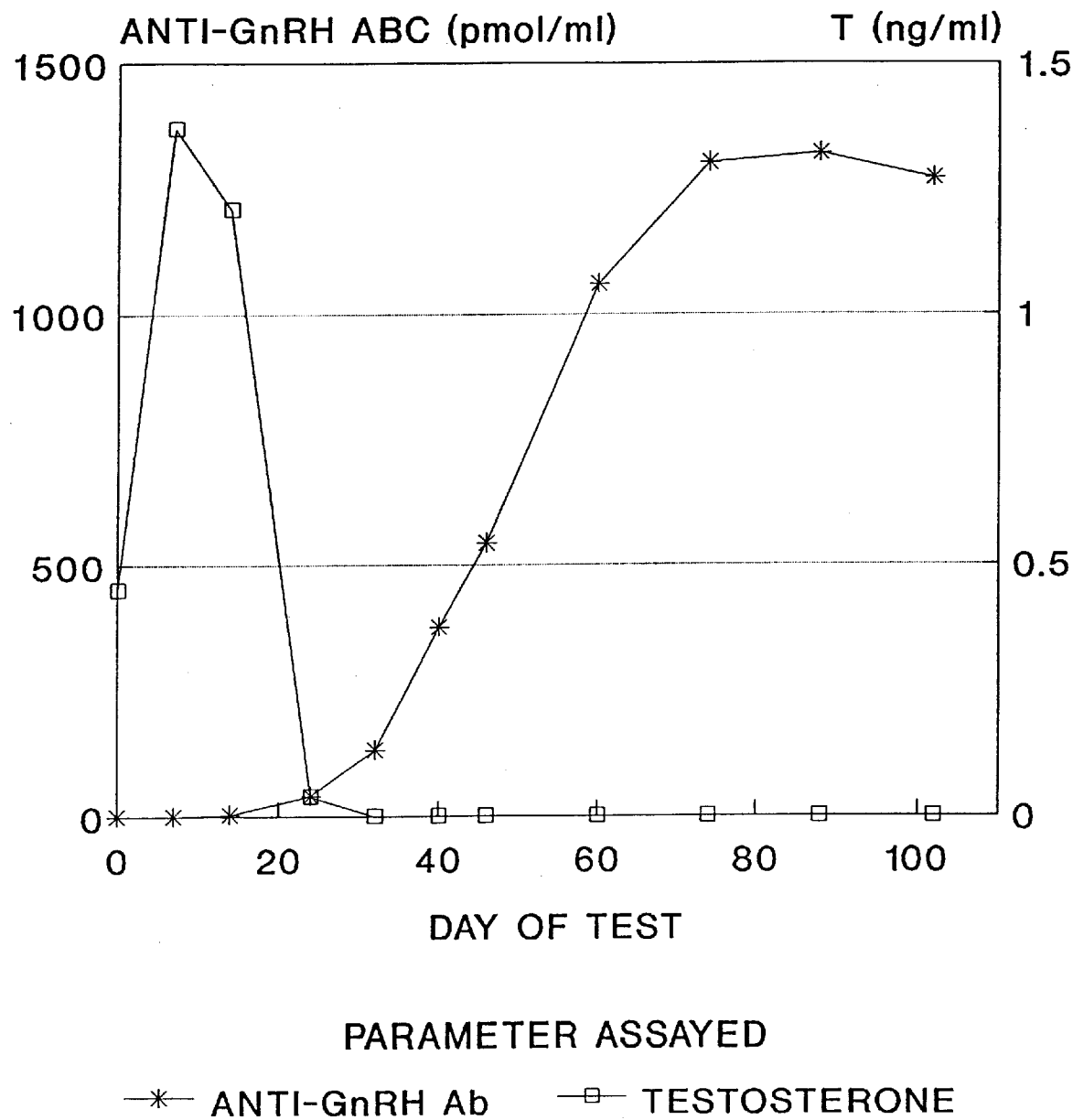
FIG. 5: Depicts antibody responses of male rabbits as measured by mean ABC with respect to days after immunization when immunized with a mixture of conjugates of peptides 1 and 2. Serum testosterone levels in these male rabbits over the course of the immunization test period are shown.

The mean ABC's measured in the sera from these three male rabbits are shown in Table 8 and in FIG. 5. As the results show, a single immunization with the DT conjugates of peptides 1 and 2 of Example 1 in the Montanide ISA 703 containing 1.8% AMS rapidly induced potent antibody responses against GnRH. These anti-GnRH responses are representative of responses induced by the peptide conjugates (individually or mixtures thereof) of this invention gated to carriers over a broad range of peptide:carrier substitution ratios and yield effective immunogens.

TABLE 7

ANTI-GnRH RESPONSES OF MICE TO PEPTIDE-CARRIER CONJUGATES WITH A DIFFERENT SUBSTITUTION RATIOS

| Conjugate number | Peptide:DT Substitution Ratio | ABC (mean ± s.e.) [pmoles/ml] | | | | | | | |
|---|---|---|---|---|---|---|---|---|---|
| | | Day 0 | Day 14 | Day 28 | Day 45 | Day 56 | Day 70 | Day 85 | Day 105 |
| 6.1 | 4.7 | 0 | 0.7 ± 0.1 | 5.1 ± 0.4 | 9.8 ± 0.5 | 9.4 ± 0.4 | 10.5 ± 0.6 | 11.0 ± 0.8 | 10.0 ± 1.0 |
| 6.1 | 13.1 | 0 | 1.8 ± 0.3 | 7.4 ± 0.6 | 9.7 ± 0.4 | 10.1 ± 0.2 | 12.2 ± 0.2 | 11.9 ± 0.2 | 11.0 ± 0.2 |
| 6.3 | 25.9 | 0 | 0.4 ± 0 | 2.1 ± 0.5 | 4.9 ± 1.0 | 5.1 ± 1.1 | 4.7 ± 1.3 | 5.7 ± 1.7 | 4.7 ± 1.6 |
| 6.4 | 5.1 | 0 | 1.7 ± 0.6 | 4.1 ± 0.6 | 4.6 ± 0.7 | 5.0 ± 0.6 | 6.8 ± 0.9 | 7.3 ± 1.2 | 6.7 ± 1.1 |
| 6.5 | 12.8 | 0 | 1.4 ± 0.1 | 4.5 ± 0.2 | 5.4 ± 0.3 | 6.1 ± 0.4 | 7.2 ± 0.2 | 8.4 ± 0.3 | 7.9 ± 0.3 |
| 6.6 | 30.1 | 0 | 1.1 ± 0.4 | 3.9 ± 0.4 | 4.6 ± 0.4 | 5.4 ± 0.4 | 6.6 ± 0.5 | 7.4 ± 0.5 | 7.0 ± 0.5 |

As the results show, significant anti-GnRH responses were induced by each of the conjugate preparations. This demonstrates that the peptides of Example 1 can be conjugated when administered with norMDP in an emulsion comprising equal parts aqueous phase and Montanide ISA 703 containing 1.8% AMS.

TABLE 8

| Day | Mean ABC (pmol/ml) (± s.e.) | Day | Mean ABC (pmol/ml) (± s.e.) |
|---|---|---|---|
| 0 | 0.02 (± 0.1) | 46 | 543 (± 85.0) |
| 7 | 0.18 (± 0) | 60 | 1061 (± 368.2) |
| 14 | 3.71 (± 0.8) | 74 | 1303.3 (± 527.6) |
| 24 | 40.3 (± 7.7) | 88 | 1320.7 (± 602.9) |
| 32 | 131.5 (± 29.1) | 102 | 1272 (± 558.1) |
| 40 | 374.7 (± 13.1) | — | — |

EXAMPLE 8

The production of gonadal steroids can be assessed as a measure of GnRH-immunogen efficacy in immunized animals. We measured testosterone levels in the serum samples obtained from the three male rabbits of Example 7. The testosterone levels were determined using a radioimmunoassay kit for testosterone determination ("Coat-a-Count", purchased from Diagnostic Products Corp., Los Angeles, Calif., USA). The results presented in Table 9 and in FIG. 5 show the immunogen induced levels of anti-GnRH antibodies that totally inhibited the production of testosterone in the male rabbits.

Testosterone was undetectable in the sera of 2 animals by day 24 of the test, and in all 3 rabbits by day 32. The drop in testosterone serum coincides with the rise in anti-GnRH Ab titer, as can be seen in FIG. 5.

TABLE 9

Testosterone Levels In Immunized Rabbits

| Day | Mean T (ng/ml) (± s.e.) | Day | Mean T (ng/ml) (± s.e.) |
|---|---|---|---|
| 0 | 0.32 (± 0.2) | 46 | 0 |
| 7 | 1.37 (± 0.1) | 60 | 0 |
| 14 | 1.21 (± 0.5) | 74 | 0 |
| 24 | 0.1 (± 0) | 88 | 0 |
| 32 | 0 | 102 | 0 |
| 40 | 0 | — | — |

---

We claim:

1. An immunogenic composition for regulating gonadal steroid hormone in a mammal comprising an anti-GnRH immunogenic conjugate consisting of an immunogenic carrier and a GnRH an immunomimic peptide extended by a spacer peptide sequence effective for immune response.

2. A method of regulating mammalian gonadal steroid hormone associated disorders or diseases comprising administering the immunogenic composition according to claim 1 to a patient in need thereof.

3. The method according to claim 2, wherein the immunogenic composition is administered as a single dosage.

4. A mammalian anti-Gn RH immunogenic conjugate comprising an immunomimic peptide attached to an immunogenic carrier by a spacer which is seven amino acids long.

* * * * *